(12) United States Patent
Brew et al.

(10) Patent No.: US 8,188,150 B2
(45) Date of Patent: May 29, 2012

(54) USE OF BETA-AMINOALCOHOLS IN THE TREATMENT OF INFLAMMATORY DISORDERS AND PAIN

(75) Inventors: John Brew, Essex (GB); Andrew Douglas Baxter, Cambridge (GB); Robin Mark Bannister, Cambridge (GB)

(73) Assignee: Biocopea Limited (GB)

( * ) Notice: Subject to any disclaimer, the term of this patent is extended or adjusted under 35 U.S.C. 154(b) by 391 days.

(21) Appl. No.: 12/282,259

(22) PCT Filed: Mar. 9, 2007

(86) PCT No.: PCT/GB2007/000816
§ 371 (c)(1),
(2), (4) Date: Mar. 29, 2009

(87) PCT Pub. No.: WO2007/102008
PCT Pub. Date: Sep. 13, 2007

(65) Prior Publication Data
US 2009/0306216 A1    Dec. 10, 2009

(30) Foreign Application Priority Data

Mar. 9, 2006  (GB) .................................. 0604822.7

(51) Int. Cl.
*A61K 31/135* (2006.01)
*A61P 1/00* (2006.01)
(52) U.S. Cl. ........................................ 514/653; 564/342
(58) Field of Classification Search .................. 514/653; 564/342
See application file for complete search history.

(56) References Cited

U.S. PATENT DOCUMENTS
4,603,019 A    7/1986   Lafon

FOREIGN PATENT DOCUMENTS
| DE | 152 814 | 6/1904 |
| EP | 0 143 711 | 6/1985 |
| FR | 2 215 954 | 8/1974 |
| FR | 2 626 879 | 8/1989 |
| JP | 53 112883 | 10/1978 |
| JP | 57 154129 | 9/1982 |
| WO | WO 01/62257 | 8/2001 |
| WO | WO 2006/092691 | 9/2006 |
| WO | WO 2007/003896 | 1/2007 |

*Primary Examiner* — Sreeni Padmanabhan
*Assistant Examiner* — Sahar Javanmard
(74) *Attorney, Agent, or Firm* — Peter D. Weinstein

(57) ABSTRACT

A compound for therapeutic use, of the formula (I), wherein $R_1$ is aryl or heteroaryl optionally substituted with $R_5$; $R_2$ is H, alkyl or $CH_2OH$ or forms part of a ring with $R_4$; $R_3$ is H, alkyl or $CH_2OH$ or forms part of a ring with $R_4$; $R_4$ is H, alkyl or (when forming part of a ring with $R_2$ or $R_3$) $CH_2$; and $R_5$ is alkyl, $CF_3$, OH, Oalkyl, OCOalkyl, $CONH_2$, CN, halogen, $NH_2$, $NO_2$, NHCHO, $NHCONH_2$, $NHSO_2Me$, $CONH_2$, or SOMe; or a salt thereof.

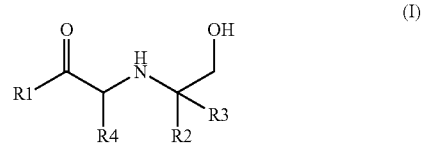

(I)

3 Claims, No Drawings

USE OF BETA-AMINOALCOHOLS IN THE TREATMENT OF INFLAMMATORY DISORDERS AND PAIN

This application is a National Stage Application of International Application Number PCT/GB2007/000816, filed Mar. 9, 2007; which claims priority to Great Britain Patent Application No. 0604822.7, filed Mar. 9, 2006, all of which are incorporated herein in their entirety.

FIELD OF THE INVENTION

This invention relates to the use of beta-aminoalcohols in the treatment of inflammatory disorders and pain

BACKGROUND OF THE INVENTION

Immune-driven inflammatory events are a significant cause of many chronic inflammatory diseases where prolonged inflammation causes tissue destruction and results in extensive damage and eventual failure of the effected organ. The cause of these diseases is unknown, so they are often called autoimmune, as they appear to originate from an individual's immune system turning on itself. Conditions include those involving multiple organs, such as systemic lupus erythematosus (SLE) and scleroderma. Other types of autoimmune disease can involve specific tissues or organs such as the musculoskeletal tissue (rheumatoid arthritis, ankylosing spondylitis), gastro-intestinal tract (Crohn's disease and ulcerative colitis), the central nervous system (Alzheimer's, multiple sclerosis, motor neurone disease, Parkinson's disease and chronic fatigue syndrome), pancreatic beta cells (insulin-dependent diabetes mellitus), the adrenal gland (Addison's disease), the kidney (Goodpasture's syndrome, IgA nephropathy, interstitial nephritis), exocrine glands (Sjogren's syndrome and autoimmune pancreatitis) and skin (psoriasis and atopic dermatitis).

In addition, there are chronic inflammatory diseases whose aetiology is more or less known but whose inflammation is also chronic and unremitting. These also exhibit massive tissue/organ destruction and include conditions such as osteoarthritis, periodontal disease, diabetic nephropathy, chronic obstructive pulmonary disease, artherosclerosis, graft versus host disease, chronic pelvic inflammatory disease, endometriosis, chronic hepatitis and tuberculosis. In these diseases, the tissue destruction often damages organ function, resulting in progressive reductions in quality of life and organ failure. These conditions are a major cause of illness in the developing world and are poorly treated by current therapies.

Inflammation of skin structures (dermatitis) is a common set of conditions which include actinic keratosis, acne rosacea, acne vulgaris, allergic contact dermatitis, angioedema, atopic dermatitis, bullous pemiphigoid, cutaneous drug reactions, erythema multiforme, lupus erythrametosus, photodermatitis, psoriasis, psoriatic arthritis, scleroderma and urticaria. These diseases are treated using a wide array of therapies, many of which have very severe side-effects.

Current disease-modifying treatments (if any) for immune-driven conditions include neutralising antibodies, cytotoxics, corticosteroids, immunosuppressants, antihistamines and antimuscarinics. These treatments are often associated with inconvenient routes of administration and severe side-effects, leading to compliance issues. Moreover, certain drug classes are only effective for certain types of inflammatory diseases, e.g. antihistamines for rhinitis.

It is known that Beta-aminoalcohols have properties which may be useful in therapy. Other such compounds are known but without any suggestion of therapeutic utility; see, for example, WO2005/069930.

SUMMARY OF THE INVENTION

Surprisingly, it has been found that certain compounds are inhibitors of cytokines and possess anti-inflammatory properties as well as reducing pain in pain conditions where cytokines are involved. According to the present invention, an inflammatory condition or pain such as acute, chronic or neuropathic pain (including, but not limited to, pain associated with cancer, surgery, arthritis, dental surgery, painful neuropathies, trauma, musculo-skeletal injury or disease, and visceral diseases) and migraine headache in mammals, can be treated by the use of a compound of general formula (I)

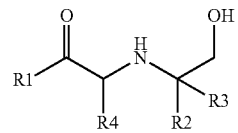

wherein
$R_1$ is aryl or heteroaryl optionally substituted with $R_5$;
$R_2$ is H, alkyl or $CH_2OH$ or forms a ring with $R_4$;
$R_3$ is H, alkyl or $CH_2OH$ or forms a ring with $R_4$;
$R_4$ is H, alkyl or (when forming part of a ring with $R_2$ or $R_3$) $CH_2$; and
$R_5$ is alkyl, $CF_3$, OH, Oalkyl, OCOalkyl, $CONH_2$, CN, halogen, $NH_2$, $NO_2$, NHCHO, $NHCONH_2$, $NHSO_2Me$, $CONH_2$ or SOMe;
or a salt thereof.

DESCRIPTION OF PREFERRED EMBODIMENTS

Compounds of formula (I) for use in the invention include (but are not limited to) novel compounds such as:
1-(4-amino-3,5-dichlorophenyl)-2-(1-hydroxy-2-methyl-propan-2-ylamino)ethanone
1-(3-chlorophenyl)-2-(1-hydroxy-2-methylpropan-2-ylamino)propan-1-one
1-(3-chlorophenyl)-2-(1-hydroxy-2-propan-2-ylamino)propan-1-one
1-(3-chlorophenyl)-2-(1-hydroxy-2-propan-2-ylamino)ethanone
1-phenyl-2-(1-hydroxy-2-propan-2-ylamino)propan-1-one
1-(2-chlorophenyl)-2-(1-hydroxy-2-methylpropan-2-ylamino)propan-1-one
1-(2-chlorophenyl)-2-(1-hydroxy-2-propan-2-ylamino)propan-1-one
1-(2-chlorophenyl)-2-(1-hydroxy-2-propan-2-ylamino)ethanone
1-(3,4-dichlorophenyl)-2-(1-hydroxy-2-methylpropan-2-γ-amino)propan-1-one
1-(3,4-dichlorophenyl)-2-(1-hydroxy-2-propan-2-ylamino)propan-1-one
1-(3,4-dichlorophenyl)-2-(1-hydroxy-2-propan-2-ylamino)ethanone
2-(1-hydroxy-2-methylpropan-2-ylamino)-1-(4-hydroxy-3-hydroxymethyl-phenyl)butan-1-one
1-(4-hydroxy-3-hydroxymethyl-phenyl)-2-(1-hydroxy-2-methylpropan-2-ylamino) ethanone 1-(4-amino-phenyl)-2-(1-hydroxy-2-methylpropan-2-ylamino)butan-1-one
1-(3,5-dimethylcarbamoyl-phenyl)-2-(1-hydroxy-2-methylpropan-2-ylamino)propan-1-one
2-(1-hydroxy-2-methylpropan-2-ylamino)-1-(phenyl)ethanone
1-(3,4-dihydroxyphenyl)-2-(1-hydroxy-2-propan-2-ylamino)propan-1-one
1-(2,3-dihydroxyphenyl)-2-(1-hydroxy-2-propan-2-ylamino)propan-1-one
1-(2,3,4-dihydroxyphenyl)-2-(1-hydroxy-2-propan-2-ylamino)propan-1-one
1-(5,6,7,8-tetrahydro-2-naphthyl)-2-(1-hydroxy-2-butan-2-ylamino)ethanone
1-(2,5-dimethoxyphenyl)-2-(1-hydroxy-2-propan-2-ylamino)propan-1-one
1-(4-hydroxy-3-ureylphenyl)-2-(1-hydroxy-2-methylpropan-2-ylamino)ethanone
1-(4-amino-3,-cyanophenyl)-2-(1-hydroxy-2-propan-2-ylamino)ethanone
1-(2-chlorophenyl)-2-(1-hydroxy-2-propan-2-ylamino)ethanone
1-(3,4-dihydroxyphenyl)-2-(1-hydroxy-2-methylpropan-2-ylamino)ethanone
1-(4-hydroxyphenyl)-2-(1-hydroxy-2-propan-2-ylamino)ethanone
1-(3,4-diacetylphenyl)-2-(1-hydroxy-2-propan-2-ylamino)ethanone
1-(3,4-dichlorophenyl)-2-(1-hydroxy-2-propan-2-ylamino)ethanone
1-(3,4-dichlorophenyl)-2-(1-hydroxy-2-methylpropan-2-ylamino)ethanone
1-(2,5-dimethoxyphenyl)-2-(1-hydroxy-2-propan-2-ylamino)propan-1-one
1-(3,4-dihydroxyphenyl)-2-(1-hydroxy-2-propan-2-ylamino)butan-1-one
1-(4-hydroxy-3-methoxyphenyl)-2-(1-hydroxy-2-propan-2-ylamino)ethanone
1-(3-hydroxyphenyl)-2-(1-hydroxy-2-propan-2-ylamino)ethanone
1-(4-nitrophenyl)-2-(1-hydroxy-2-propan-2-ylamino)ethanone
1-(3-hydroxyquinolin-5-yl)-2-(1-hydroxy-2-propan-2-ylamino)ethanone
1-(4-hydroxy-3-methanesulphonamidephenyl)-2-(1-hydroxy-2-propan-2-ylamino)ethanone
1-(4-methanesulphonamidephenyl)-2-(1-hydroxy-2-propan-2-ylamino)ethanone
1-(2-chloro-4-hydroxyphenyl)-2-(1-hydroxy-2-methylpropan-2-ylamino)ethanone
1-(2-fluorophenyl)-2-(1-hydroxy-2-methylpropan-2-ylamino)ethanone
1-(3-fluorophenyl)-2-(1-hydroxy-2-methylpropan-2-ylamino)ethanone
1-(4-fluorophenyl)-2-(1-hydroxy-2-methylpropan-2-ylamino)ethanone
1-(4-fluorophenyl)-2-(1-hydroxy-2-methylpropan-2-ylamino)ethanone
1-(4-bromophenyl)-2-(1-hydroxy-2-methylpropan-2-ylamino)propan-1-one
1-(4-bromophenyl)-2-(1-hydroxy-2-methylpropan-2-ylamino)propan-1-one
1-(3,5-ditertbutylcarbonyloxyphenyl)-2-(1-hydroxy-2-methylpropan-2-ylamino)ethanone
1-(3,5-dihydroxyphenyl)-2-(1-hydroxy-2-propan-2-ylamino)ethanone
1-(3,5-dihydroxyphenyl)-2-(1-hydroxy-2-propan-2-ylamino)propan-1-one
1-(3-chloro-4-amino-5-trifluoromethylphenyl)-2-(1-hydroxy-2-propan-2-ylamino)propan-1-one
1-(2-naphthalenyl)-2-(1-hydroxy-2-propan-2-ylamino)ethanone It is understood that the invention refers to salts, e.g. the hydrochloride of compounds (I). The compounds may also be provided as metabolites and pro-drugs thereof. The compounds are chiral, and the invention includes substantially single diastereomers and enantiomers of (I). Aryl and heteroaryl groups are know, and typically have up to 12 atoms.

The compounds of formula (I) according to the invention are used to treat inflammatory diseases including, but not exclusive to, autoimmune diseases involving multiple organs, such as systemic lupus erythematosus (SLE) and scleroderma, specific tissues or organs such as the musculoskeletal tissue (rheumatoid arthritis, ankylosing spondylitis), gastrointestinal tract, (Crohn's disease and ulcerative colitis), the central nervous system (Alzheimers, Multiple sclerosis, motor neurone disease, Parkinson's disease and chronic fatigue syndrome), pancreatic beta cells (insulin dependent diabetes mellitus), the adrenal gland (Addison's disease), the kidney (Goodpasture's syndrome, IgA nephropathy, interstitial nephritis) exocrine glands (Sjogrens syndrome and autoimmune pancreatitis) and skin (psoriasis and atopic dermatitis), chronic inflammatory diseases such as osteoarthritis, periodontal disease, diabetic nephropathy, chronic obstructive pulmonary disease, artherosclerosis, graft versus host disease, chronic pelvic inflammatory disease, endometriosis, chronic hepatitis and tuberculosis, IgE mediated (Type I) hypersensitivities such as rhinitis, asthma, anaphylaxis, dermatitis and ophthalmic conditions. Dermatitis conditions include; actinic keratosis, acne rosacea, acne vulgaris, allergic contact dermatitis, angioedema, atopic dermatitis, bullous pemiphigoid, cutaneous drug reactions, erythema multiforme, lupus erythrametosus, photodermatitis, psoriasis, psoriatic arthritis, scleroderma and urticaria. Ophthalmic conditions include age related macular degeneration, diabetic retinopathy, choroidal neovascular membrane, cystoid macular edema, epi-retinal membrane, macular hole, dry eye and uveitis.

These compounds may be used according to the invention when the patient is also administered or in combination with another therapeutic agent selected from corticosteroids (examples including cortisol, cortisone, hydrocortisone, dihydrocortisone, fludrocortisone, prednisone, prednisolone, deflazacort, flunisolide, beconase, methylprednisolone, triamcinolone, betamethasone, and dexamethasone), disease modifying anti-rheumatic drugs (DMARDs) (examples including, azulfidine, aurothiomalate, bucillamine, chlorambucil, cyclophosphamide, leflunomide, methotrexate, mizoribine, penicillamine and sulphasalazine), immunosuppressants (examples including azathioprine, cyclosporin, mycophenolate,) COX inhibitors (examples including aceclofenac, acemetacin, alcofenac, alminoprofen, aloxipirin, amfenac, aminophenazone, antraphenine, aspirin, azapropazone, benorilate, benoxaprofen, benzydamine, butibufen, celecoxib, chlorthenoxacine, choline salicylate, chlometacin, dexketoprofen, diclofenac, diflunisal, emorfazone, epirizole, etodolac, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, mefenamic acid, metamizole, mofebutazone, mofezolac, nabumetone, naproxen, nifenazone, oxametacin, phenacetin, pipebuzone, pranoprofen, propyphenazone, proquazone, rofecoxib, salicylamide, salsalate, sulindac, suprofen, tiaramide, tinoridine, tolfenamic acid, zomepirac) neutralising antibodies (examples including, etanercept and infliximab), antibiotics (examples including, doxycycline and minocycline).

Compounds of formula (I) exhibit analgesic activity in animal models. The activity of these compounds may be determined by the use of the appropriate in vivo assay.

This invention also relates to a method of treatment for patients (including man and/or mammalian animals raised in the dairy, meat or fur industries or as pets) suffering from chronic, acute or neuropathic pain; and more specifically, a method of treatment involving the administration of the analgesic of formula (I) as the active constituent.

Accordingly, the compounds of formula (I) can be used among other things in the treatment of pain conditions such as acute and chronic pain (as well as, but not limited to, pain associated with cancer, surgery, arthritis, dental surgery, trauma, musculo-skeletal injury or disease, visceral diseases) and migraine headache. Additionally the painful conditions can be neuropathic (post-herpetic neuralgia, diabetic neuropathy, drug induced neuropathy, HIV mediated neuropathy, sympathetic reflex dystrophy or causalgia, fibromyalgia, myofacial pain, entrapment neuropathy, phantom limb pain, trigeminal neuralgia. Neuropathic conditions include central pain related to stroke, multiple sclerosis, spinal cord injury, arachnoiditis, neoplasms, syringomyelia, Parkinson's and epilepsia.

It will often be advantageous to use compounds of formula (I) in combination with another drug used for pain therapy. Such another drug may be an opiate or a non-opiate such as baclofen. Especially for the treatment of neuropathic pain, coadministration with gabapentin is preferred. Other compounds that may be used include acetaminophen, a non-steroidal anti-inflammatory drug, a narcotic analgesic, a local anaesthetic, an NMDA antagonist, a neuroleptic agent, an anti-convulsant, an anti-spasmodic, an anti-depressant or a muscle relaxant.

Any suitable route of administration can be used. For example, any of oral, topical, parenteral, ocular, rectal, vaginal, inhalation, buccal, sublingual and intranasal delivery routes may be suitable. The dose of the active agent will depend on the nature and degree of the condition, the age and condition of the patient and other factors known to those skilled in the art. A typical dose is 1.0-100 mg given one to three times per day.

The compounds of the invention may be prepared via a multistep synthetic route of a type familiar to those skilled in the art, and it is assumed that functional groups present in the molecules can be protected and deprotected as needed. The synthesis begins with a substituted acetophenone or analogue which is reacted initially with bromine to give the bromo derivative, and then the amino alcohol to generate the target molecule. The final compounds are generally isolated via precipitation which may require purification via a technique such as recrystallisation.

The following Examples illustrate the preparation of compounds of the invention.

EXAMPLE 1

1-(4-Amino-3,5-dichlorophenyl)-2-(1-hydroxy-2-methylpropan-2-ylamino)ethanone (3)

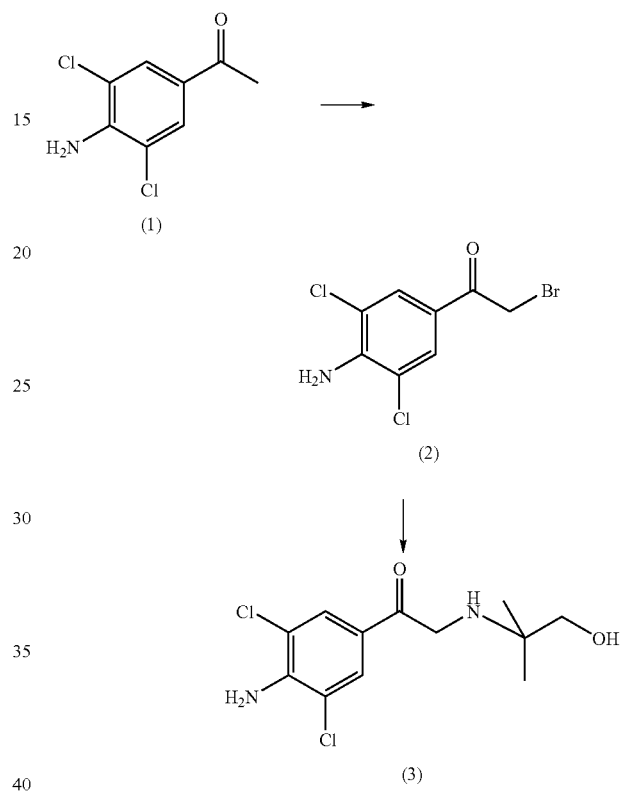

Bromo-(-4-amino-3,5-dichloro)acetophenone (2)

Bromine (63 ml, 1.22 mol) was added to a mixture of 4-amino-3,5-dichloroacetophenone (1) (250 g, 1.22 mol) in CHCl$_3$ (3 L ml) at room temperature. The mixture was stirred for 1 h then EtOH (500 ml) was added. The mixture was cooled to 0° C. and stirred for 1 h. The precipitate was filtered and air-dried (4.7 g, 67%).

$^1$H NMR (400 MHz, DMSO): 4.77 (2H, s), 6.61 (2H, bs), 7.86 (2H, s); $^{13}$C NMR (100 MHz, DMSO): 63.39, 117.89, 128.57, 129.75, 146.17, 195.99.

1-(4-Amino-3,5-dichlorophenyl)-2-(1-hydroxy-2-methylpropan-2-ylamino)ethanone (3)

2-Amino-2-methyl-propan-1-ol (180 ml, 2.49 mol) was added to a mixture of bromo-(-4-amino-3,5-dichloro)acetophenone (2) (237 g, 0.83 mol) in chloroform (650 ml). The mixture was stirred at room temperature for 2 h, then water (380 ml) was added. The mixture was stirred for 1 h, and then the solid was filtered. The solid was triturated with water (1 L) to give the desired compound (3) (223 g, 91%).

$^1$H NMR (400 MHz, DMSO): 0.94 (6H, s), 3.18 (2H, d J=4.4 Hz), 3.93 (2H, s), 4.55 (1H, m), 6.40 (2H, s), 7.84 (2H, s), $^{13}$C NMR (100 MHz, DMSO): 24.21, 48.87, 53.73, 68.52, 117.92, 124.57, 125.79, 128.62, 146.07, 195.30; LC-MS: 291, 292, 293 (M+H$^+$).

EXAMPLE 2

2-(1-hydroxy-2-methylpropan-2-ylamino)-1-(3-chlorophenyl)propan-1-one (4)

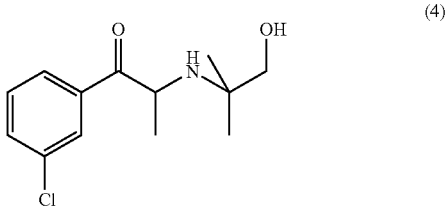

(4)

Bromo-3'-chloropropiophenone

Bromine (6.07 ml, 0.12 mol) was added to a solution of 3'-chloropropiophenone (20 g, 0.12 mol) in chloroform (250 ml) at room temperature. The reaction was followed by TLC in DCM. When all of the starting material was consumed the mixture was washed with a saturated solution of sodium bicarbonate. The organic phase was dried over magnesium sulphate, filtered and evaporated. Recrystallisation from chloroform gives the desired compound in 60% yield as a pale yellow solid (18 g, 73 mmol).

$^1$H NMR (400 MHz, CDCl$_3$): 7.99 (1H, m), 7.89 (1H, m), 7.55 (1H, m), 7.43 (m), 5.21 (1H, q J=6.5 HZ), 1.9 (3H, J=6.5 Hz)

2-(1-hydroxy-2-methylpropan-2-ylamino)-1-(3-chlorophenyl)propan-1-one (4)

2-Amino-1-methyl-propan-1-ol (14 ml, 0.15 mol) was added to α-bromo-3'chloro propiophenone (18 g, 73 mmol) in suspension in chloroform (50 ml), with two crystals of sodium iodide. The reaction was heated under reflux overnight. After filtration the organic phase was extracted twice with a 2M HCl solution (2×100 ml). The aqueous phase wash washed with DCM then neutralised with sodium carbonate. The aqueous layer was extracted with DCM. The organic phase was dried over magnesium sulphate, filtered and evaporated. Recrystallisation from chloroform gives the desired compound in 55% yield as a white solid (10.2 g, 40 mmol).

$^1$H NMR (400 MHz, CDCl$_3$): 7.57 (1H, m), 7.27-7.26 (2H, m), 3.77-3.74 (1H, m), 3.37-3.34 (1H, m), 3.14-3.11 (1H, m), 1.37 (3H, s), 1.04 (3H, s), 0.76 (3H, s). $^{13}$C NMR (100 MHz, CHCl$_3$): 16.23, 22.69, 27.06, 49.85, 53.41, 69.33, 95.91, 124.52, 126.62, 128.04, 129.34, 134.05, 144.11. LC-MS: 256 (M+H$^+$).

The following Assays illustrate the utility of the invention.
Beta2 Agonism Functional Assay Guinea-pig trachea ring preparations were suspended in Kreb's solution containing indomethacin. After 15 minutes stabilisation, the preparations were repeated contracted using carbachol and simultaneously treated with increasing cumulative doses test compounds (0.1 nM to 0.1 μM). Beta2 agonism for each test compound was determined by its dose dependant inhibition of carbachol stimulated tracheal muscle twitch.

Compound (3) was a very poor beta2 agonist, with an IC50 of 13 μM.
LPS Mouse Assay 7 week-old Balb C ByJ mice (24-28 g) were administered, either by i.p. (5 ml/kg) or oral (10 ml/kg) administration, with vehicle or test article. 30 minutes later these animals were challenged with an intraperitoneal injection of 1 mg/kg LPS. 2 hours after LPS challenge blood samples were collected under light isoflurane anaesthesia into normal tubes by retroorbital puncture. Samples were allowed to clot at room temperature and then spun at 6000 g for 3 min at 4° C. Serum was stored at −20° C. until use. Serum TNFα and IL-10 levels were analysed in duplicate by ELISA technique.

Compound (3) had strong inhibitory effects on TNFα and potentiating effects on IL-10. These effects are unlikely to be due to beta2 agonism.
Carrageenan Paw Assay Fasted (18 hour) male Wistar rats (105-130 g) were weighed and a basal mercury plethysmometer reading was taken of the right hind paw by submerging the paw in the mercury up to the tibiotarsal joint. Subsequently, vehicles, reference items and test articles were administered by oral gavage (10 ml/kg). Half an hour after treatment 0.1 ml of 2% carrageenan in 0.9% saline was injected into the subplanatar area of the right hind paw. The right paw was measured again with the plethysmometer at 1, 2, 3, 4 and 5 hours after carrageenan administration.

Compound (3) had a dose-dependant inhibitory effect on inflammation induced by carrageenan paw injection.

The invention claimed is:

1. A method for the treatment of an inflammatory bowel disease wherein said method comprises administering, to a subject in need of such treatment, a compound of the formula:

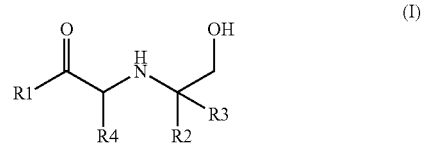

(I)

wherein R$_1$ is aryl optionally substituted with R$_5$;
R$_2$ is H, alkyl or CH$_2$OH;
R$_3$ is H, alkyl or CH$_2$OH;
R$_4$ is H, alkyl; and
R$_5$ is alkyl, CF$_3$, OH, Oalkyl, OCOalkyl, CONH$_2$, CN, halogen, NH$_2$, NO$_2$, NHCHO, NHCONH$_2$, NHSO$_2$Me, CONH$_2$ or SOMe;
or a salt thereof.

2. The method, according to claim 1, used to treat ulcerative colitis or Crohn's disease.

3. The method, according to claim 1, wherein the compound is α-[(1,1-dimethyl-2-hydroxyethyl)amino]4-amino-3,5-dichloroacetophenone.

* * * * *